(12) United States Patent
Matsukata et al.

(10) Patent No.: US 10,392,329 B2
(45) Date of Patent: Aug. 27, 2019

(54) METHOD FOR CONDENSING WATER-SOLUBLE ORGANIC MATTER AND DEVICE FOR CONDENSING WATER-SOLUBLE ORGANIC MATTER

(71) Applicants: WASEDA UNIVERSITY, Shinjuku-ku, Tokyo (JP); JX NIPPON OIL & ENERGY CORPORATION, Chiyoda-ku, Tokyo (JP); MITSUBISHI CHEMICAL CORPORATION, Chiyoda-ku, Tokyo (JP); HITACHI ZOSEN CORPORATION, Osaka-shi, Osaka (JP); CHIYODA CORPORATION, Yokohama-shi, Kanagawa (JP)

(72) Inventors: Masahiko Matsukata, Tokyo (JP); Kenichi Kawazuishi, Yokohama (JP); Kenichi Mimura, Yokohama (JP)

(73) Assignees: WASEDA UNIVERSITY, Tokyo (JP); MITSUBISHI CHEMICAL CORPORATION, Tokyo (JP); HITACHI ZOSEN CORPORATION, Osaka (JP); CHIYODA CORPORATION, Kanagawa (JP)

( * ) Notice: Subject to any disclaimer, the term of this patent is extended or adjusted under 35 U.S.C. 154(b) by 413 days.

(21) Appl. No.: 14/889,834

(22) PCT Filed: Apr. 30, 2014

(86) PCT No.: PCT/JP2014/061957
§ 371 (c)(1),
(2) Date: Nov. 6, 2015

(87) PCT Pub. No.: WO2014/185269
PCT Pub. Date: Nov. 20, 2014

(65) Prior Publication Data
US 2016/0107964 A1 Apr. 21, 2016

(30) Foreign Application Priority Data

May 17, 2013 (JP) ................................. 2013-105620

(51) Int. Cl.
*C07C 29/82* (2006.01)
*B01D 53/22* (2006.01)
(Continued)

(52) U.S. Cl.
CPC .............. *C07C 29/82* (2013.01); *B01D 3/145* (2013.01); *B01D 53/229* (2013.01);
(Continued)

(58) Field of Classification Search
CPC ...... C07C 29/82; B01D 3/145; B01D 53/229; B01D 61/364
See application file for complete search history.

(56) References Cited

U.S. PATENT DOCUMENTS

| 4,405,409 A | 9/1983 | Tusel |
| 2009/0057224 A1* | 3/2009 | Huang ................. B01D 53/268 |
| | | 210/640 |

(Continued)

FOREIGN PATENT DOCUMENTS

| JP | 58-55001 A | 4/1983 |
| JP | 1-155928 A | 6/1989 |

(Continued)

OTHER PUBLICATIONS

EPO, Office Action dated Jun. 14, 2017 in corresponding EP Application No. 14797464 total 5 pages.
(Continued)

*Primary Examiner* — Yate' K Cutliff
(74) *Attorney, Agent, or Firm* — Masuvalley & Partners

(57) ABSTRACT

A method and a device for condensing a water-soluble organic matter, which can collect a highly concentrated
(Continued)

water-soluble organic matter, save energy, and reduce cost of the device by reducing a membrane area.

According to the present invention, the permeability ratio of a vapor-permeation separation membrane disposed at least immediately before a final outlet on a non-permeation side in the separation membrane device is lower than those of the other vapor-permeation separation membranes while a hybrid process combining distillation by the distillation column with membrane separation by the separation membrane devices including a plurality of vapor-permeation separation membranes is used and energy saving performance is maintained. Therefore, a highly concentrated and condensed component of a water-soluble organic matter is obtained. In addition, it is possible to reduce a membrane area of the vapor-permeation separation membranes in the whole separation membrane devices and to provide a technology leading to cost reduction.

8 Claims, 8 Drawing Sheets

(51) Int. Cl.
- *B01D 3/14* (2006.01)
- *C07C 29/76* (2006.01)
- *B01D 61/36* (2006.01)
- *C07C 29/80* (2006.01)

(52) U.S. Cl.
CPC ......... *B01D 61/364* (2013.01); *B01D 61/366* (2013.01); *C07C 29/76* (2013.01); *C07C 29/80* (2013.01); *B01D 2257/70* (2013.01); *Y02P 20/126* (2015.11); *Y02P 20/57* (2015.11); *Y02P 20/572* (2015.11)

(56) References Cited

U.S. PATENT DOCUMENTS

| | | |
|---|---|---|
| 2011/0130598 A1 | 6/2011 | Huang |
| 2012/0190091 A1* | 7/2012 | Huang ................ B01D 53/228 435/161 |
| 2013/0015052 A1 | 1/2013 | Vane |

FOREIGN PATENT DOCUMENTS

| | | |
|---|---|---|
| JP | 2004-89882 A | 3/2004 |
| JP | 2012-110832 A | 6/2012 |

OTHER PUBLICATIONS

ISA/JP Examiner Mitsuko Saito, International Search Report dated Jul. 22, 2014 in International Application No. PCT/JP2014/061957, total 5 pages including translation.

EPO, EP Patent Office Action dated Dec. 20, 2017 in corresponding EP Patent Application No. 14797464.6.

EPO, EP Patent Office Action dated Mar. 8, 2018 in corresponding EP Patent Application No. 14797464.6.

* cited by examiner

METHOD FOR CONDENSING WATER-SOLUBLE ORGANIC MATTER AND DEVICE FOR CONDENSING WATER-SOLUBLE ORGANIC MATTER

RELATED APPLICATIONS

This application is the U.S. National Phase of and claims priority to International Patent Application No. PCT/JP2014/061957, International Filing Date Apr. 30, 2014, entitled Method For Condensing Water-Soluble Organic Matter And Device For Condensing Water-Soluble Organic Matter (as translated), which claims benefit of Japanese Application No. JP2013-105620, filed May 17; all of which are incorporated herein by reference in their entireties.

TECHNICAL FIELD

The present invention relates to a method and a device for condensing a water-soluble organic matter. More specifically, the present invention relates to a method and a device for condensing a water-soluble organic matter by a hybrid process combining distillation with membrane separation.

BACKGROUND ART

A technology is provided, in which a raw material of a water-soluble organic matter which forms an azeotrope with water and the azeotrope of which with water has a lower boiling point than water, such as isopropyl alcohol (hereinafter, also referred to as "IPA"), or a water-soluble organic matter having a lower boiling point than water is dehydrated by a process combining separation by distillation using a distillation column with membrane separation using a vapor-permeation separation membrane (hereinafter, also referred to as a hybrid process) (for example, refer to Patent Literature 1). It is known that such a hybrid process can save energy more largely than conventional dehydration only by distillation.

Pressure distillation or atmospheric pressure distillation is used as a method for separation by distillation. When the pressure distillation is combined with a separation membrane, column top vapor of a distillation column is treated directly by a vapor-permeation separation membrane. On the other hand, when the atmospheric pressure distillation is combined with a separation membrane, column top vapor is pressurized by a vapor compressor, and then is treated by a vapor-permeation separation membrane. The hybrid process combining the pressure distillation with the vapor-permeation separation membrane is industrialized, for example, in dehydration of bioethanol.

When an organic matter is dehydrated and condensed so as to have a high purity using a current hybrid process, high selectivity, high permeability, or the like with respect to water is required as performance of a vapor-permeation separation membrane. For example, when IPA is dehydrated and condensed to about 99.0% by mass of the total mass, in general, a vapor-permeation separation membrane having a permeability ratio (also referred to as permeance ratio) between IPA and water in the order of several hundreds and having permeability (also referred to as permeance) of water of about $10^{-6}$ mol/m$^2$·Pa·s or more, is necessary. The higher the permeability ratio is, the higher the energy saving performance of the whole process is.

CITATION LIST

Patent Literature

Patent Literature 1: JP 2012-110832 A

SUMMARY OF INVENTION

Technical Problem

However, in a case of making the condensation degree of IPA very high so as to be, for example, 99.9% by mass or more, when a vapor-permeation separation membrane having high membrane performance is used, a large membrane area is disadvantageously necessary as a whole separation membrane device including the vapor-permeation separation membrane. This is because most of the components on a permeation side of the vapor-permeation separation membrane becomes water due to the high selectivity of the vapor-permeation separation membrane, and a driving force (difference in partial pressure of water between a raw material side and the permeation side) for membrane separation becomes smaller. The present inventors have focused on this fact and achieved the present invention.

Here, in order to improve the driving force, it is possible in a certain range to raise the pressure on the raw material side or reduce the pressure on the permeation side. However, when the pressure on the raw material side is raised, it is necessary to raise the pressure of the whole distillation column or the discharge pressure of a compressor, and device cost or power of the compressor is disadvantageously increased. When the pressure on the permeation side is reduced, the condensing temperature of water on the permeation side reaches 0° C., and for example, water may be frozen disadvantageously. In addition, there is a limit on reducing the pressure on the permeation side to raise a vacuum degree. Improvement is necessary.

The present invention has been achieved to solve the above problems. An object of the present invention is to provide a method and a device for condensing a water-soluble organic matter by a hybrid process combining distillation with membrane separation. By the method, it is possible to collect a highly concentrated water-soluble organic matter and save energy even when the concentration of the water-soluble organic matter is very high, and to achieve low cost of a device by reducing the membrane area.

Solution to Problem

In order to solve the above problems, the method for condensing a water-soluble organic matter according to the present invention is a method for condensing a water-soluble organic matter by distillation and membrane separation. The method includes a distillation step and a membrane separation step. In the distillation step, a raw material including a mixture of water and a water-soluble organic matter having a lower boiling point than water or a mixture of water and a water-soluble organic matter which forms an azeotrope with water and the azeotrope of which with water has a lower boiling point than water, is input into a distillation column and the raw material is distilled. In the membrane separation step, column top vapor obtained in the distillation step is introduced into a separation membrane device having a plurality of stages of vapor-permeation separation membranes through which water vapor goes selectively, and a water-soluble organic matter having a required concentration of more than 99.0% by mass is obtained from a final outlet on a non-permeation side in the separation membrane device by membrane separation of the vapor-permeation separation membrane. When the permeability of water is referred to as $K_W$ and the permeability of a water-soluble organic matter is referred to as $K_A$ in the vapor-permeation separation membrane, the permeability ratio $K_W/K_A$ of a vapor-permeation separation membrane disposed at least immediately before the final outlet on the non-permeation side in the separation membrane device is lower than those of the other vapor-permeation separation membranes.

In the method for condensing a water-soluble organic matter according to the present invention, the vapor-permeation separation membrane having a lower permeability ratio than the other vapor-permeation separation membranes is disposed in a range of ⅛ to ½ from the final outlet on the non-permeation side in the separation membrane device of the whole of the plurality of stages of vapor-permeation separation membranes in the above-described present invention.

In the method for condensing a water-soluble organic matter according to the present invention, the vapor-permeation separation membrane having a lower permeability ratio than the other vapor-permeation separation membranes condenses a water-soluble organic matter in the separation membrane device from an intermediate concentration of 99.0% by mass or more to the required concentration in the above-described present invention.

In the method for condensing a water-soluble organic matter according to the present invention, the vapor-permeation separation membrane having a lower permeability ratio than the other vapor-permeation separation membranes has a higher permeability of water than those of the other vapor-permeation separation membranes in the above-described present invention.

In the method for condensing a water-soluble organic matter according to the present invention, at least a part of permeation components of the separation membrane device is introduced into the distillation column in the above-described present invention.

In the method for condensing a water-soluble organic matter according to the present invention, the required concentration is 99.9% by mass or more in the above-described present invention.

In the method for condensing a water-soluble organic matter according to the present invention, the water-soluble organic matter is at least one selected from the group consisting of isopropanol, ethanol, methanol, and butanol in the above-described present invention.

The device for condensing a water-soluble organic matter according to the present invention is a device for condensing a water-soluble organic matter by distillation and membrane separation. The device includes a distillation column and a separation membrane device. Into the distillation column, a raw material including a mixture of water and a water-soluble organic matter having a lower boiling point than water or a mixture of water and a water-soluble organic matter which forms an azeotrope with water and the azeotrope of which with water has a lower boiling point than water, is input and the raw material is distilled therein. The separation membrane device has a plurality of vapor-permeation separation membranes into which column top vapor in the distillation column is introduced and through which water vapor goes selectively to obtain a water-soluble organic matter having a required concentration of more than 99.0% by mass from a final outlet on a non-permeation side by membrane separation of the vapor-permeation separation membrane. When the permeability of water is referred to as $K_W$ and the permeability of a water-soluble organic matter is referred to as $K_A$ in the vapor-permeation separation membrane, the permeability ratio $K_W/K_A$ of a vapor-permeation separation membrane disposed at least immediately before the final outlet on the non-permeation side in the separation membrane device is lower than those of the other vapor-permeation separation membranes.

In the device for condensing a water-soluble organic matter according to the present invention, the vapor-permeation separation membrane having a lower permeability ratio than the other vapor-permeation separation membranes has a higher permeability of water than those of the other vapor-permeation separation membranes in the above-described present invention.

Advantageous Effects of Invention

According to the present invention, the permeability ratio of a vapor-permeation separation membrane disposed at least immediately before the final outlet on the non-permeation side in the separation membrane device is lower than those of the other vapor-permeation separation membranes in the separation membrane device while a hybrid process combining distillation with membrane separation is used and energy saving performance is maintained. Therefore, a highly concentrated and condensed component of a water-soluble organic matter is obtained. In addition, it is possible to reduce a membrane area of the vapor-permeation separation membrane in the whole separation membrane device and to provide a method and a device for condensing a water-soluble organic matter, leading to reduction in cost of the device.

DESCRIPTION OF EMBODIMENTS

Hereinafter, examples of embodiments of the present invention will be described based on the drawings.

(I) Configuration of Device 1 for Condensing Water-Soluble Organic Matter:

Hereinafter, a method for condensing a water-soluble organic matter according to the present invention using the device 1 for condensing a water-soluble organic matter illustrated in FIG. 1 will be described.

Figure 1:
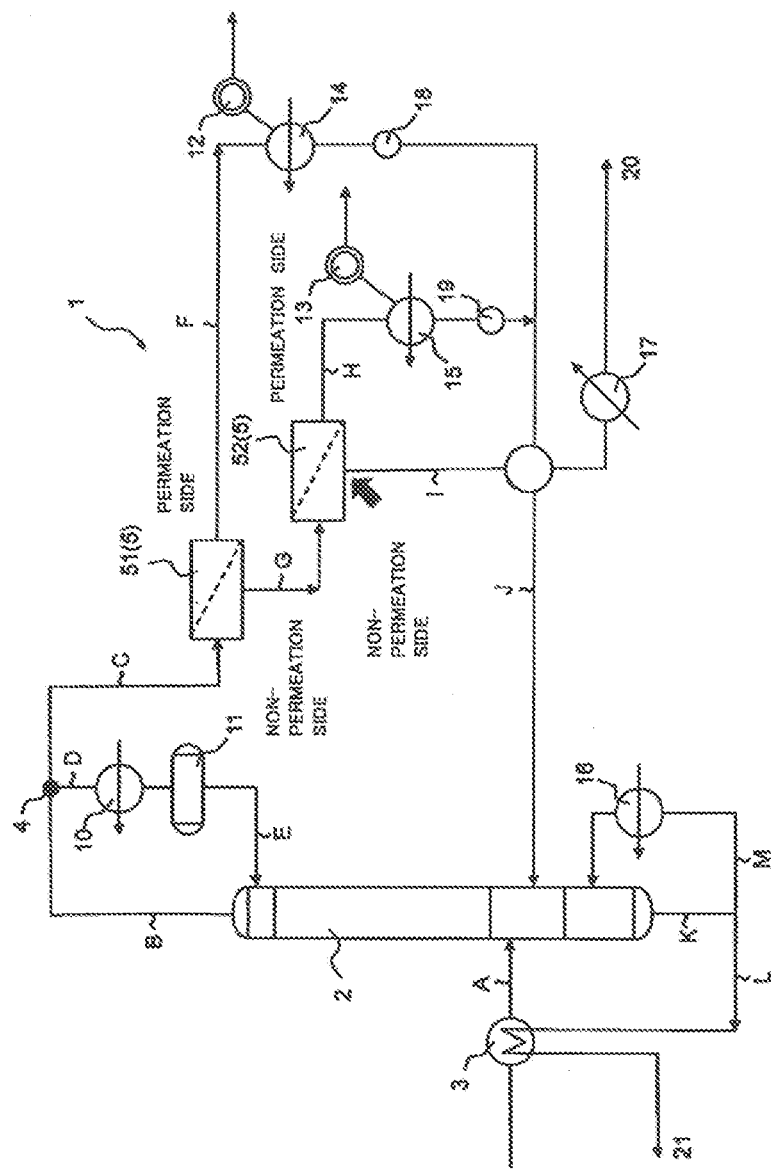
FIG. 1 is a schematic diagram illustrating an aspect of a device for condensing a water-soluble organic matter according to the present invention.

FIG. 1 is a schematic diagram illustrating an aspect of the device 1 for condensing a water-soluble organic matter according to the present invention. The device 1 for condensing a water-soluble organic matter according to the present invention illustrated in FIG. 1 (hereinafter, also referred to as "condensing device 1") includes a distillation column 2 and separation membrane devices 51 and 52 having a plurality of stages of vapor-permeation separation membranes 5 as basic components, and condenses a water-soluble organic matter from a raw material including a mixture of water and the water-soluble organic matter by distillation and membrane separation.

(a) Distillation Step:

In the condensing device 1 illustrated in FIG. 1, a mixture including water and a water-soluble organic matter which passes through a path A and is to be condensed, is input (introduced) into the distillation column 2 as a raw material. The raw material includes a mixture of water and a water-soluble organic matter having a lower boiling point than water or a mixture of water and a water-soluble organic matter which forms an azeotrope with water and the azeotrope of which with water has a lower boiling point than water. Examples of the water-soluble organic matter mainly include alcohol. Examples of the water-soluble organic matter having a lower boiling point than water include methanol. Examples of the water-soluble organic matter which forms an azeotrope with water and the azeotrope of which with water has a lower boiling point than water include ethanol, isopropanol (IPA), and butanol. These water-soluble organic matters can be used.

The distillation column 2 separates the raw material including a mixture of water and a water-soluble organic matter, input from the path A, into column top vapor including a water-soluble organic matter in a gas state and a column bottom liquid including water in a liquid state. The distillation column 2 is not particularly limited as long as the distillation column 2 is suitable for a distillation operation. Examples thereof include a tray-type distillation column. A part of the liquid at the bottom of the distillation column 2 becomes vapor by being heated by a reboiler 16, and goes up in the column while exchanging heat with liquid flowing down in the column. Therefore, most of the components of the vapor at the column bottom is water, but the concentration of a water-soluble organic matter is large near the column top. A remaining portion of the liquid extracted from the column bottom is extracted as the column bottom liquid.

The distillation column 2 can perform various kinds of distillations such as pressure distillation or atmospheric pressure distillation. The number of trays of the distillation column 2 is not particularly limited, and can be determined appropriately according to a required concentration spec of a water-soluble organic matter, or the like. In the distillation column 2, a raw material is preferably condensed to a water-soluble organic matter approximately at 85.0% by mass or more. For example, when a required concentration spec (specification) is more than 99.0% by mass and less than 99.9% by mass, a raw material is preferably condensed to a water-soluble organic matter at 85.0% by mass or more and less than 99.0% by mass. When the required concentration spec is 99.9% by mass or more, a raw material is preferably condensed to a water-soluble organic matter at 85.0% by mass or more and less than 99.9% by mass. However, there is no particular limitation to this range.

The column top vapor output from the distillation column 2 passes through a path B, reaches a junction 4, and branches to a path C side and a path E side. In the present embodiment, the column top vapor from the junction 4 to the path C side is sent to the separation membrane devices 51 and 52. The column top vapor to the path E side is sent back to the distillation column 2 to be refluxed.

The column top vapor which has been separated in the junction 4 and will be sent back to the distillation column 2 through the paths D and E is introduced into a cooler 10 to be cooled and condensed. The column top vapor cooled and condensed by the cooler 10 passes through a condenser drum (also referred to as reflux drum) 11, passes through the path E, and is refluxed into the column top of the distillation column 2 again.

(b) Membrane Separation Step:

The column top vapor which has passed through the junction 4 passes through the path C and is introduced into the separation membrane device 51. The separation membrane device 51 and the separation membrane device 52 as a subsequent stage thereof each have a plurality of stages of vapor-permeation separation membranes 5 through which water vapor of the introduced column top vapor goes selectively. The vapor-permeation separation membrane 5 (also referred to as vapor separation membrane) makes a water vapor component (permeation component) go therethrough and extracts the water vapor component, and separates the remaining component (non-permeation component) in a state of vapor and sends the remaining component to a path.

As illustrated in FIG. 1, in the condensing device 1 according to the present embodiment, the two separation membrane devices 51 and 52 are disposed. In paths F and H on the permeation sides of the separation membrane devices 51 and 52, coolers 14 and 15 are disposed, respectively. It is possible to reduce the pressure on the permeation side by cooling and condensing the water vapor which has gone through the membrane. In addition, in the paths F and H, vacuum pumps 12 and 13 are disposed, respectively, in order to maintain the reduced pressure on the permeation side. It is possible to make the water vapor component go through the vapor-permeation separation membranes 5 included in the separation membrane devices 51 and 52 preferentially using a difference in pressure (difference in partial pressure) between the reduced pressure state caused by the coolers 14 and 15 on the permeation side and the introduction side (the path C side in the separation membrane device 51 and the path G side in the separation membrane device 52) as a driving force. The vacuum pumps 12 and 13 reduce the pressure through the coolers 14 and 15 which cool and condense water vapor which goes through the membrane using cooling water.

As described above, in order to secure the driving force, it is necessary to reduce the pressure on the permeation side, but the condensation temperature is also lowered. Therefore, a chilled cooler using chilled cooling as a refrigerant may be used as the coolers 14 and 15.

As for the permeability ratio in the vapor-permeation separation membrane 5, for example, when the permeability of water $K_{-W}$ is $10^{-6}$ mol/m$^2$·Pa·s or more, the permeability of a water-soluble organic matter $K_{-A}$ (mol/m$^2$·Pa·s) should be adjusted to obtain a desired permeability. A membrane area is determined by the permeability and a treatment amount in the condensing device 1, but a range thereof is not particularly limited.

The kind of the vapor-permeation separation membrane 5 should be determined appropriately according to the kind of the components included in a water-soluble organic matter, the temperature of vapor input and distilled, the pressure, or the like. Examples thereof include an organic (polymer) membrane such as a polyimide membrane, a polyvinyl alcohol membrane, or a cellulose acetate membrane, and an inorganic membrane such as a zeolite membrane, a carbon membrane, or a porous ceramic membrane. In the present invention, it is possible to use a water vapor-permeation separation membrane which makes water (water vapor) go therethrough selectively and can separate the water (water vapor) from other components efficiently. Particularly when the raw material is a two-component system of water and a water-soluble organic matter such as isopropanol, it is possible to use a zeolite membrane, a polyimide membrane, or the like which makes water (water vapor) go therethrough and separates the water (water vapor) from isopropanol or the like in a vapor state as a water vapor-permeation separation membrane. It is possible to dehydrate and condense a water-soluble organic matter efficiently and selectively from a mixture of water and a water-soluble organic matter such as isopropanol. Examples of the zeolite membrane include a membrane using zeolite, such as an A type membrane, a Y type, a mordenite type, or a chabazite type.

The configuration of the vapor-permeation separation membrane 5 (pore diameter, shape, porous or non-porous, or the like) is not particularly limited, and should be determined appropriately according to the kind of the components included in a raw material, the temperature of a water-soluble organic matter input, the pressure, or the like, similarly to the above-described kind of the vapor-permeation separation membrane 5. The vapor-permeation separation membrane 5 may be used in a multitubular form such as a so-called separation membrane module.

When the vapor-permeation separation membrane 5 is a separation membrane module, a separation membrane module of one stage (one path) or two stages (two paths) (a pair of vapor-permeation separation membranes 5 correspond to one stage (one path)) is generally used. However, as the number of stage increases, a raw material can be condensed more highly, but pressure loss is increased. Therefore, for example, the separation membrane devices 51 and 52 having four to eight stages in total are preferably used.

When, the permeability of water is referred to as $K_W$ and the permeability of a water-soluble organic matter is referred to as $K_A$ in the vapor-permeation separation membrane 5 in the separation membrane device at the subsequent stage (the separation membrane device 52 in the present embodiment, the same hereinafter) of the two separation membrane devices 51 and 52, the permeability ratio is referred to as $K_W/K_A$. At this time, in the present embodiment, the permeability ratio of the vapor-permeation separation membrane 5 disposed at least immediately before the final outlet on the non-permeation side in the separation membrane device 52 is made to be lower than those of the other vapor-permeation separation membranes 5 in the separation membrane device 51 and 52. By such a configuration, low device cost (small membrane area) can be achieved while high energy saving performance and a high yield of a highly concentrated water-soluble organic matter are maintained due to the hybrid process. In the present invention, the "final outlet in the separation membrane device 52" means a port (position indicated by a bold arrow in FIG. 1) to take out a product in the separation membrane device 52. The "vapor-permeation separation membrane 5 disposed immediately before" means a vapor-permeation separation membrane 5 closest to the final outlet (port to take out the product).

In the present invention, the separation membrane device 52 is for obtaining a water-soluble organic matter having a desired concentration (required concentration) more than 99.0% by mass from the final outlet on the non-permeation side. Therefore, as for the vapor-permeation separation membranes 5 included in the separation membrane devices 51 and 52, the permeability ratio of a vapor-permeation separation membrane (hereinafter, also referred to as "other vapor-permeation separation membrane" or "vapor-permeation separation membrane having a high permeability ratio") 5 other than the vapor-permeation separation membrane 5 disposed at least immediately before the final outlet is, for example, approximately 100 or more and is preferably selected from a range of 200 to 500, and should be determined in accordance with the vapor-permeation separation membrane 5 disposed at least immediately before the final outlet. On the other hand, the permeability ratio of the vapor-permeation separation membrane (hereinafter, also referred to as "vapor-permeation separation membrane having a low permeability ratio") 5 disposed at least immediately before the final outlet in the separation membrane device 52 is made to be lower than those of the other vapor-permeation separation membranes 5, and is, for example, preferably selected from a range of 50 to 200.

Here, a reason why the above effects are exhibited by making the permeability ratio of the vapor-permeation separation membrane 5 at least at the last stage in the separation membrane device 52 lower than those of the other vapor-permeation separation membranes, will be described using isopropyl alcohol (IPA) as an example of a water-soluble organic matter.

Figure 2:
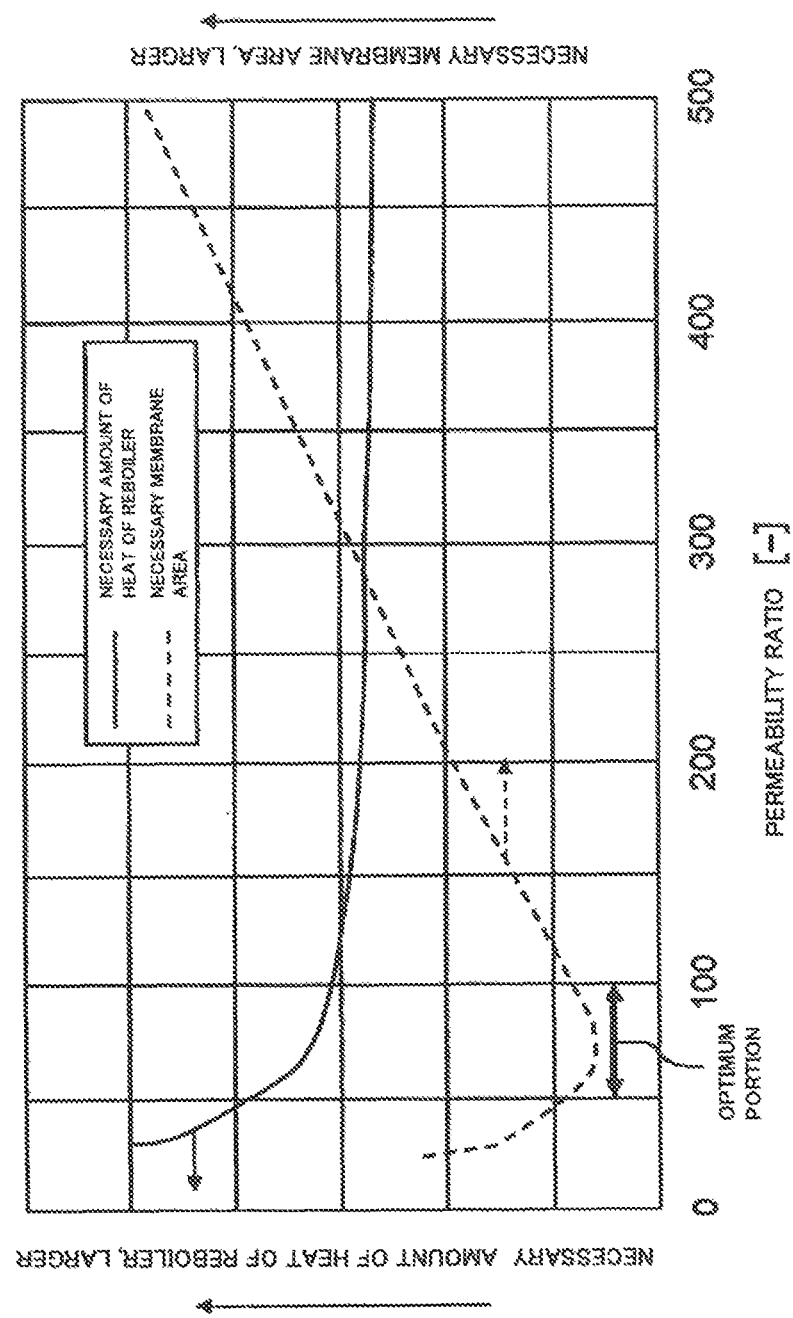
FIG. 2 is a diagram illustrating a relation between a permeability ratio and a necessary amount of heat of a reboiler and a relation between the permeability ratio and a necessary membrane area of a vapor-permeation separation membrane.
Figure 3:
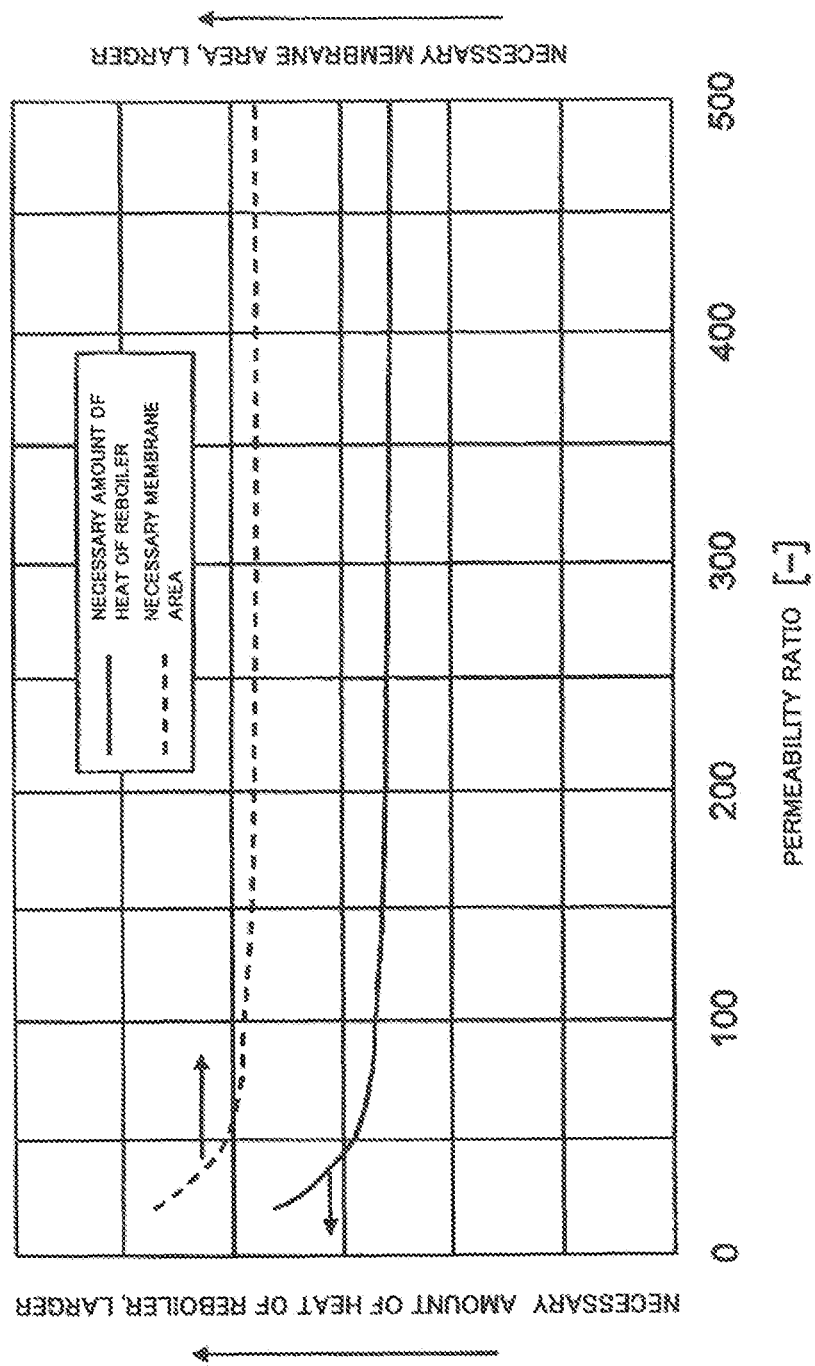
FIG. 3 is a diagram illustrating a relation between a permeability ratio and a necessary amount of heat of a reboiler and a relation between the permeability ratio and a necessary membrane area of a vapor-permeation separation membrane.

FIG. 2 is a diagram illustrating a relation between a permeability ratio and a necessary amount of heat of the reboiler 16 and a relation between a permeability ratio and a necessary membrane area of the vapor-permeation separation membrane 5 when the concentration IPA at the final outlet of the vapor-permeation separation membrane 5 included in the separation membrane device 52 is more than 99.0% by mass (for example, 99.9% by mass) in the condensing device 1 in FIG. 1. The permeability ratio in FIG. 2 illustrates a case where the permeability ratios of all the vapor-permeation separation membranes 5 included in the separation membrane devices 51 and 52 were changed uniformly. FIG. 2 and FIG. 3 described below illustrate results of simulation analysis of optimum conditions or the like when IPA was used as a water-soluble organic matter, a mixture of IPA and water was used as a raw material, and the concentration of IPA at the final outlet of the vapor-permeation separation membrane 5 included in the separation membrane device 52 was set to a desired concentration (for example, in FIG. 2, a concentration of 99.9% by mass or the like more than 99.0% by mass, and in FIG. 3, a concentration of 99.0% by mass or the like lower than that in FIG. 2). As illustrated in FIG. 2, when the concentration of IPA at the final outlet of the vapor-permeation separation membrane 5 included in the separation membrane device 52 is more than 99.0% by mass, a necessary amount of heat of the reboiler 16 with respect to the permeability ratio is decreased as the permeability ratio is increased. In other words, as the permeability ratio becomes smaller, the necessary amount of heat is increased. This is based on the following fact. That is, in order to obtain highly concentrated IPA more than 99.0% by mass, it is necessary to collect IPA leaked to the permeation side of the vapor-permeation separation membrane 5 due to the use of the vapor-permeation separation membrane 5 having a low permeability ratio and low performance by recycling the IPA to the distillation column 2.

On the other hand, as for a necessary membrane area of the vapor-permeation separation membrane 5 with respect to the permeability ratio, a portion having a minimum membrane area (optimum portion) occurs in a range of the permeability ratio of 50 to 100. This phenomenon occurs because of the following. That is, the membrane area of the vapor-permeation separation membrane 5 for condensing a water-soluble organic matter to a high concentration at a level of more than 99.0% by mass is increased. Meanwhile, when the concentration spec becomes as low as 99.0% by mass or less, a driving force can be secured sufficiently, and therefore this portion becomes unnecessary (refer to FIG. 3 described below). Hereinafter, more detailed description will be given.

As illustrated in FIG. 2, when the permeability ratio is more than 100, as the permeability ratio is higher, a larger membrane area of the vapor-permeation separation membrane 5 is required. A reason why a larger membrane area is required as the permeability ratio is higher while the permeability ratio is more than 100 is that a driving force (difference in partial pressure of water between the raw material side and the permeation side) immediately before the final outlet in the vapor-permeation separation membrane 5 becomes smaller.

In order to increase the driving force immediately before the final outlet, a method of reducing the pressure on the permeation side is considered. However, by this method, water on the permeation side cannot be condensed disadvantageously in some cases.

On the other hand, in order to increase the driving force, application of a vapor-permeation separation membrane 5 having a low permeability ratio is considered. Application of the vapor-permeation separation membrane 5 having a low permeability ratio increases loss of IPA to the permeation side. However, the loss of IPA to the permeation side can reduce a partial pressure of water on the permeation side, and contributes to increase in the driving force. Here, when the vapor-permeation separation membrane 5 having a low permeability ratio is applied, the loss of IPA to the permeation side is increased as described above, and an amount of heat input is increased as illustrated in FIG. 2, disadvantageously. Meanwhile, when the vapor-permeation separation membrane 5 having a low permeability ratio is applied only for the vapor-permeation separation membrane 5 immediately before the final outlet in the separation membrane devices 51 and 52, increase in the loss of IPA or increase in the amount of heat input is small, but a large driving force is obtained, and a remarkably large amount of permeation component (water) goes through the membrane. It is considered that further condensation can be expected and the membrane area of the whole separation membrane devices 51 and 52 can be suppressed to be small.

FIG. 2 indicates that the permeability ratio has an optimum portion having a minimum membrane area when a condensation purity of IPA is more than 99.0% by mass, particularly 99.9% by mass or more. In the present embodiment, by using the existence of such an optimum portion, the vapor-permeation separation membrane 5 having a low permeability ratio is used for the vapor-permeation separation membrane 5 at least immediately before the final outlet on the non-permeation side in the separation membrane devices 52 to increase the driving force and thereby condense a water-soluble organic matter highly.

In the present invention, as for the vapor-permeation separation membranes 5 in the separation membrane devices 51 and 52, the permeability ratio of the vapor-permeation separation membrane 5 at least on the final outlet side is lower than those of the other vapor-permeation separation membranes 5. The vapor-permeation separation membrane (vapor-permeation membrane having a low permeability ratio) 5 having a lower permeability than the other vapor-permeation separation membranes 5 is preferably disposed in a predetermined range from the final outlet on the non-permeation side of the separation membrane device 51 or 52. By such a configuration, a difference in partial pressure of water can be maintained smoothly even when the concentration of a water-soluble organic matter is highly condensed, and the above effects can be exhibited efficiently. As such a predetermined range, for example, a range of ⅛ to ½ from the final outlet is preferable and a range of ⅛ to ¼ is particularly preferable, with respect to all the plurality of stages of vapor-permeation separation membranes 5 including the other vapor-permeation separation membranes 5. Here, when the vapor-permeation separation membranes 5 occupying the range of ⅛ to ½ (or ¼) from the final outlet are referred to as latter vapor-permeation separation membranes 5 and the other vapor-permeation separation membranes 5 (other vapor-permeation separation membranes 5) are referred to as former vapor-permeation separation membranes 5, the present invention includes a case where the permeability ratios of most (for example, stages corresponding to 90% or 95%) of the latter vapor-permeation separation membranes 5 are lower than those of most (for example, stages corresponding to 90% or 95%) of the former vapor-permeation separation membranes 5, or the like. In addition, the present invention also includes a case where the permeability ratios of the former vapor-permeation separation membranes 5 gradually become lower toward the final outlet on the non-permeation side and the permeability ratios of the latter vapor-permeation separation membranes 5 gradually become lower toward the final outlet on the non-permeation side (including a case where the permeability ratio of the last (the last stage of) separation membrane of the former vapor-permeation separation membranes 5 is the same as that of the first (the first stage of) separation membrane of the latter vapor-permeation separation membranes 5), or the like as long as the permeability ratios of the latter vapor-permeation separation membranes 5 are lower than those of the former vapor-permeation separation membranes 5 as a whole (for example, lower as an average).

In the present invention, the vapor-permeation separation membrane 5 at least on the final outlet side or the vapor-permeation separation membrane 5 having a low permeability ratio disposed in the above-described predetermined range (for example, ⅛ to ½ described above) condenses a water-soluble organic matter from a predetermined intermediate concentration of 99.0% by mass or more to a desired concentration. The reason is as follows. That is, when the vapor-permeation separation membrane 5 having a high permeability ratio is used for all the vapor-permeation separation membranes 5 in the separation membrane devices 51 and 52, a driving force (difference in partial pressure) of water cannot be obtained after condensation proceeds. Meanwhile, by using the vapor-permeation separation membrane 5 having a low permeability ratio at least on the final outlet side or in a predetermined range from the final outlet, a small amount of IPA is lost, but the driving force is maintained. Permeation thereby further occurs in comparison with use of the vapor-permeation separation membrane 5 having a high permeability ratio of water, and condensation further proceeds. It is considered that the vapor-permeation separation membrane 5 having a low permeability ratio further condenses a water-soluble organic matter condensed by the vapor-permeation separation membrane 5 having a high permeability ratio in this way.

The vapor-permeation separation membrane 5 having a low permeability ratio preferably has a permeability of water equal to or more than that of the vapor-permeation separation membrane 5 having a high permeability ratio. This is because the membrane area of the vapor-permeation separation membrane 5 having a low permeability ratio can be reduced. In general, an amount of water to be dehydrated is determined by a concentration spec of a desired product. Therefore, the larger the permeation mount of water per unit area is, the smaller the membrane area of the vapor-permeation separation membrane 5 can be. On the other hand, when the permeability ratio is low, an amount of a water-soluble organic matter leaked to the permeation side is large. Therefore, disadvantageously, a product amount is decreased and the concentration of the water-soluble organic matter in water is increased. However, a necessary membrane area is almost determined by the permeability of water. Therefore, the membrane area can be reduced by making the permeability of water of the vapor-permeation separation membrane 5 having a low permeability ratio equal to or more than that of the vapor-permeation separation membrane 5 having a high permeability ratio.

The optimum portion illustrated in FIG. 2 becomes smaller gradually as the condensation concentration of IPA is lowered. When the condensation concentration of IPA is lowered from 99.0% by mass or the like to 99.0% by mass or less, the optimum portion disappears. FIG. 3 is a diagram illustrating a relation between a permeability ratio and a necessary amount of heat of the reboiler 16 and a relation between a permeability ratio and a necessary membrane area of the vapor-permeation separation membrane 5 when the concentration of IPA at the final outlet of the vapor-permeation separation membrane 5 included in the separation membrane device 52 is 99.0% by mass in the condensing device 1 in FIG. 1.

As illustrated in FIG. 3, as the permeability ratio becomes higher (as the permeability of IPA becomes smaller with the proviso that the permeability of water is constant), the necessary amount of heat of the reboiler 16 and the membrane area of the vapor-permeation separation membrane 5 tend to be reduced, and a minimum portion of the membrane area with respect to the permeability ratio, as in FIG. 2, disappears. From FIGS. 2 and 3, it is considered that the above-described existence of the optimum portion (minimum portion) appears only in the case where IPA has a high concentration more than 99.0% by mass at the final outlet of the vapor-permeation separation membrane 5 as illustrated in FIG. 2, and the existence of the optimum portion appears more significantly as the concentration becomes higher. In view of this, the present invention is effective when the concentration of a water-soluble organic matter obtained from the final outlet on the non-permeation side of the vapor-permeation separation membrane 5 (separation membrane device 52) is required to be as extremely high as 99.9% by mass or more as a desired concentration more than 99.0% by mass.

In the present invention, dehydration and condensation are performed by the separation membrane devices 51 and 52 as described above. A non-permeation component (water-soluble organic matter) having a concentration of more than 99.0% by mass of the components separated by the separation membrane devices 51 and 52 passes through a path I, is cooled and condensed in a cooler 17, and then is output outside the system from a collecting unit 20 to be collected.

On the other hand, a permeation component mainly including water of the components separated by the separation membrane devices 51 and 52 may include a small amount of non-permeation component (water-soluble organic matter) depending on the degree of selectivity of the vapor-permeation separation membranes 5 included in the separation membrane devices 51 and 52. In the condensing device 1 according to the present embodiment, the coolers 14 and 15 for condensing a permeation component in a vapor state and pumps 18 and 19 are disposed in the paths F and H through which the permeation component in a vapor state passes. The permeation component condensed in the coolers 14 and 15 passes through a path J and is introduced into the distillation column 2 again. In the present invention, by using a vapor-permeation separation membrane 5 having a low permeability ratio for the vapor-permeation separation membrane 5 disposed immediately before the final outlet, a loss amount of a water-soluble organic matter to the permeation side is increased, and therefore the yield of the water-soluble organic matter may be lowered disadvantageously. However, by introducing condensed water of the permeation component into the distillation column 2, it is possible to dehydrate the water-soluble organic matter so as to have a high purity and a high yield nearly without spoiling energy saving performance of the whole process.

The column bottom liquid separated in the distillation column 2, including water in a liquid state but hardly including a water-soluble organic matter, passes through a path K connected to the column bottom of the distillation column 2 and a path L. Thereafter, the column bottom liquid is introduced into a heat exchanger 3 disposed in the path A, is used for preheating or vaporizing a raw material, and is output outside the system from a collecting unit 21 to be collected. A part of the column bottom liquid output outside the system passes through a path M, is then subjected to heat exchange in the reboiler 16, and is sent back to the distillation column 2.

According to the present invention described above, the permeability ratio of the vapor-permeation separation membrane 5 disposed at least immediately before the final outlet on the non-permeation side in the separation membrane device 52 is lower than those of the other vapor-permeation separation membranes 5 in the separation membrane devices 51 and 52 while a hybrid process combining distillation by the distillation column 2 with membrane separation by the separation membrane devices 51 and 52 including a plurality of vapor-permeation separation membranes 5 is used and energy saving performance is maintained. Therefore, a highly concentrated and condensed component of a water-soluble organic matter is obtained. In addition, it is possible to reduce a membrane area of the vapor-permeation separation membrane 5 in the whole separation membrane devices 51 and 52 and to provide a technology leading to reduction in cost of the device.

The aspect described above indicates an aspect of the present invention, and the present invention is not limited to the above-described embodiment. Needless to say, modification or improvement in a range in which the configuration of the present invention is included and the object and effects thereof can be achieved is included in the contents of the present invention. When the present invention is performed, a specific configuration, shape, or the like may be another configuration, shape, or the like without a problem in a range in which the object and effects of the present invention can be achieved. The present invention is not limited to the above-described embodiment. Modification or improvement in a range in which the object of the present invention can be achieved is included in the present invention.

For example, in the above-described embodiment, as illustrated in FIG. 1, the two separation membrane devices 51 and 52 having the vapor-permeation separation membranes 5 are disposed. However, the number of the separation membrane devices 51 and 52 is arbitrary, and should be determined appropriately according to a concentration spec required for a water-soluble organic matter, or the like.

In the above-described embodiment, as illustrated in FIG. 1, a permeation component in a vapor state is condensed, then passes through a path J, and is introduced into the distillation column 2 again. However, a part of the permeation component may be introduced into the distillation column 2 again, and the permeation component does not necessarily have to be introduced into the distillation column 2.

In the condensing device 1 illustrated in FIG. 1, a preheater may be disposed between the distillation column 2 and the heat exchanger 3, and a raw material input may be preheated to an appropriate temperature. As the preheater, it is possible to use a preheater using a known heating means such as steam preheating.

In addition, when the present invention is performed, a specific configuration, shape, or the like may be another configuration or the like in a range in which the object of the present invention can be achieved.

EXAMPLES

Hereinafter, the present invention will be described more specifically based on Examples or the like, but is not limited in any way to such Examples or the like.

Reference Example 1

Figure 4:
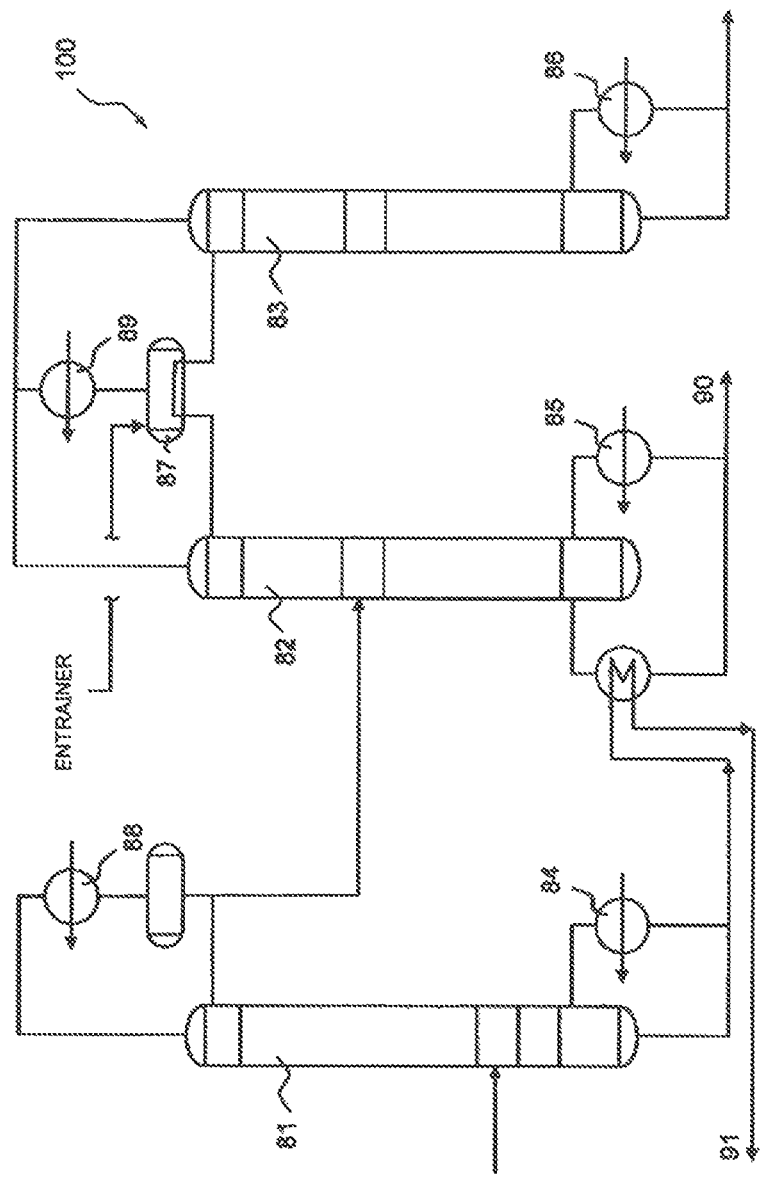
FIG. 4 is a schematic diagram illustrating a device for condensing a water-soluble organic matter used in Reference Example 1.

FIG. 4 illustrates the configuration of a device for condensing a water-soluble organic matter 100 in Reference Example 1 used as an indicator. FIG. 4 is a schematic diagram illustrating the configuration of the device for condensing a water-soluble organic matter 100 in Reference Example 1. The condensing device 100 does not include a separation membrane device (vapor-permeation separation membrane) but includes three distillation columns 81 to 83, reboilers 84 to 86, a liquid-liquid separator 87, and coolers 88 and 89. Main specifications of the condensing device 100 illustrated in FIG. 4 are as follows.

(Specifications of Device)

Distillation column (azeotropic column) 81: column diameter 100 mm, height 20 m, filling ⅝ ball ring made of SUS304

Distillation column (dehydration column) 82: column diameter 50 mm, height 20 m, filling ⅝ ball ring made of SUS304

Distillation column (wastewater stripper) 83: column diameter 50 mm, height 20 m, filling ⅝ ball ring made of SUS304

The kind of entrainer: hexane, cyclohexane, benzene

In order to confirm a reference amount of heat, an operation of condensing IPA was performed using the condensing device 100 illustrated in FIG. 4 such that the concentration of IPA at the final outlet of a collecting unit 90 had a high purity (99.9% by mass or more) with the proviso that isopropanol (IPA) was used as a water-soluble organic matter, a mixture of isopropanol and water was used as a raw material, the concentration of IPA at the time of input was 13.0% by mass, and the concentration of water was 87.0% by mass. In this case, an amount of heat necessary for the condensing operation (amount of heat input into the three reboilers 84 to 86) was subjected to simulation analysis using a process simulation software.

Specifically, the raw material including a mixture of IPA and water was input into the distillation column (azeotropic column) 81 as the first column, and was condensed such that the concentration of IPA became that of a predetermined azeotropic mixture. The azeotropic mixture obtained from the column top of the distillation column (azeotropic column) 81 was sent to the distillation column (dehydration column) 82 as the second column, and water was extracted from the column top by an entrainer to thereby obtain IPA having a high purity from the collecting unit 90 at the bottom of the distillation column (dehydration column) 82. The entrainer and water at the column top were condensed, and then were liquid-liquid separated by the liquid-liquid separator 87. The water phase after the liquid-liquid separation was treated by the distillation column (wastewater stripper) 83 as the third column. Water included in the azeotropic mixture was taken out from the column bottom to be obtained in a collecting unit 91. An amount of heat necessary for condensation was determined by simulation analysis, and a total amount of heat determined was defined to be 1.0 as an indicator. Out of 1.0, an amount of heat input into the reboiler 84 was 0.65, an amount of heat input into the reboiler 85 was 0.32, and an amount of heat input into the reboiler 86 was 0.03.

Analysis Examples 1 to 3

Next, operations of condensing IPA were performed using the condensing device 1 illustrated in FIG. 1 such that the concentration of IPA at the final outlet of the separation membrane device 52 was a desired concentration more than 99.9% by mass (Analysis Example 1), 99.9% by mass (Analysis Example 2), or 99.0% by mass (Analysis Example 3) according to the above-described (a) distillation step and (b) membrane separation step, with the proviso that isopropanol (IPA) was used as a water-soluble organic matter, a mixture of isopropanol and water was used as a raw material, the concentration of IPA at the time of input was 13.0% by mass, and the concentration of water was 87.0% by mass. In this case, simulation analysis was performed. Basic conditions of the distillation column 2 in Analysis Examples 1 to 3 are as follows.

(Basic Conditions)

Pressure in path C: 400 kPaG

Temperature of column top vapor in path C: 126° C.

Concentration of IPA in path C: 85.0% by mass

Pressure in path F (permeation side in separation membrane device 51): 10 kPaA

Pressure in path H (permeation side in separation membrane device 52): 2 kPaA

Cooler 14: cooling with cold water

Cooler 15: chilled cooling (Specifications of Distillation Column 2)

Distillation column (azeotropic column) 2: column diameter 100 mm, height 20 m, filling ⅝ ball ring made of SUS304

Figure 7:
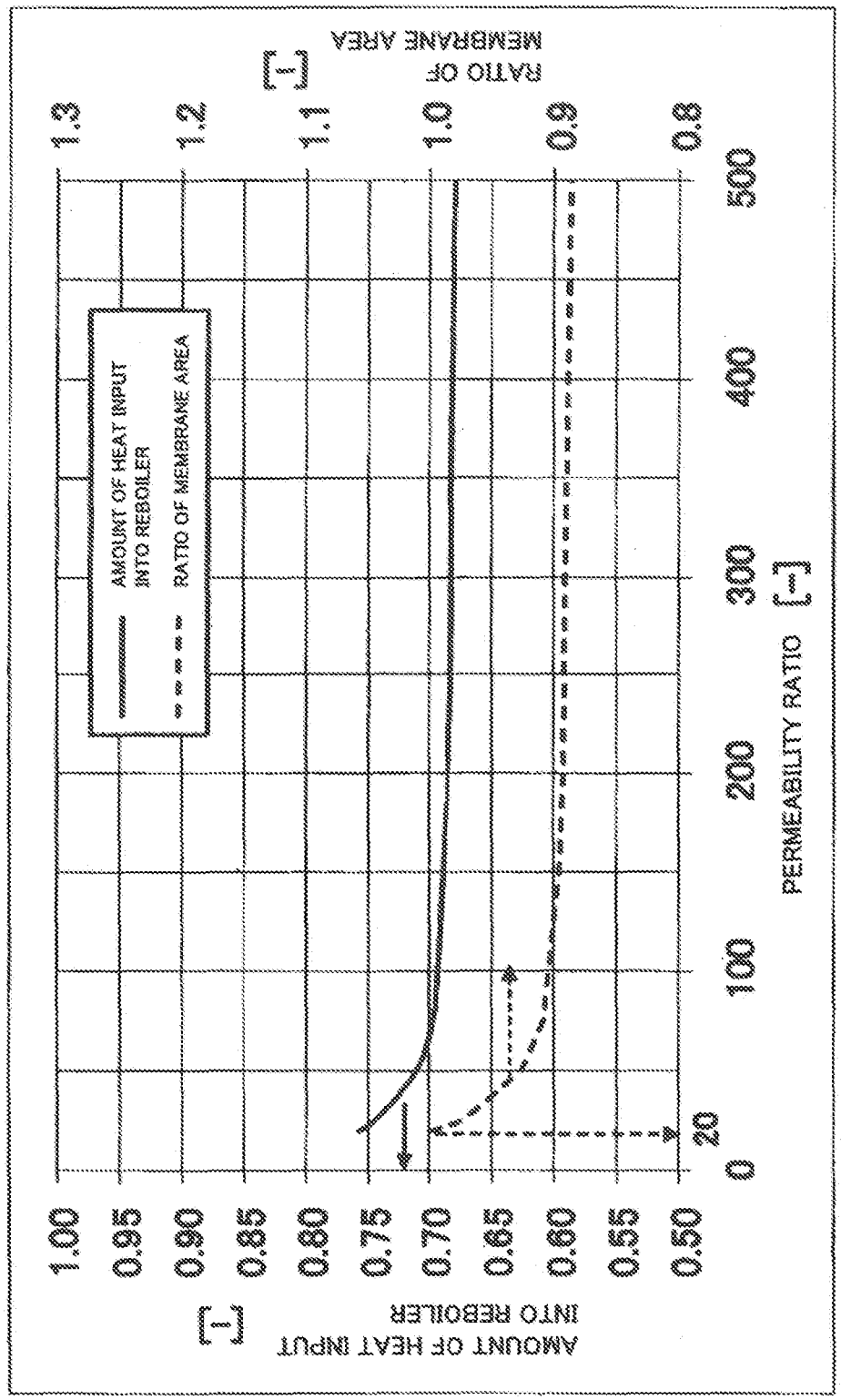
FIG. 7 is a diagram illustrating results in Analysis Example 3.

In the analysis, as for the separation membrane devices 51 and 52 (two devices) of the condensing device 1 illustrated in FIG. 1, it was assumed that a separation membrane module having one vapor-permeation separation membrane for one stage (one path) as the vapor-permeation separation membrane 5 was used, and that the separation membrane device 51 had two stages (two paths), the separation membrane device 52 had four stages (four paths), and six stages (six paths) were included in total. In the case where the above-described condensing operation was performed while all the permeability ratios of the vapor-permeation separation membranes 5 were the same, the "amount of heat input into the reboiler of the distillation column with respect to the necessary amount of heat determined in Reference Example 1" (hereinafter, also simply referred to as "amount of heat input into the reboiler", the same in FIGS. 5 and 8) and the "ratio of a membrane area with respect to the membrane area of the vapor-permeation separation membrane in the case of permeability ratio=20" (hereinafter, also simply referred to as "ratio of membrane area", the same in FIGS. 5 and 8), with respect to the "permeability ratio of the vapor-permeation separation membrane in the separation membrane device", were subjected to simulation analysis using a process simulation software. The results are shown in FIGS. 5 and 7.

As described above, the total amount of heat input into the three reboilers 84 to 86 of the condensing device 100 illustrated in Reference Example 1 (total amount of heat input) was 1.0. The amount of heat input was calculated based on this total amount of heat input. The permeability ratio=20 was an initial value. Similarly, the permeability ratio was increased from the initial value (=20) and results were calculated based on this initial value. The permeability ratio was adjusted such that the permeability ratio of water $K_W$ was fixed to $5 \times 10^{-6}$ mol/m²·Pa·s and the permeability ratio of IPA $K_A$ (mol/m²·Pa·s) was changed.

Figure 5:
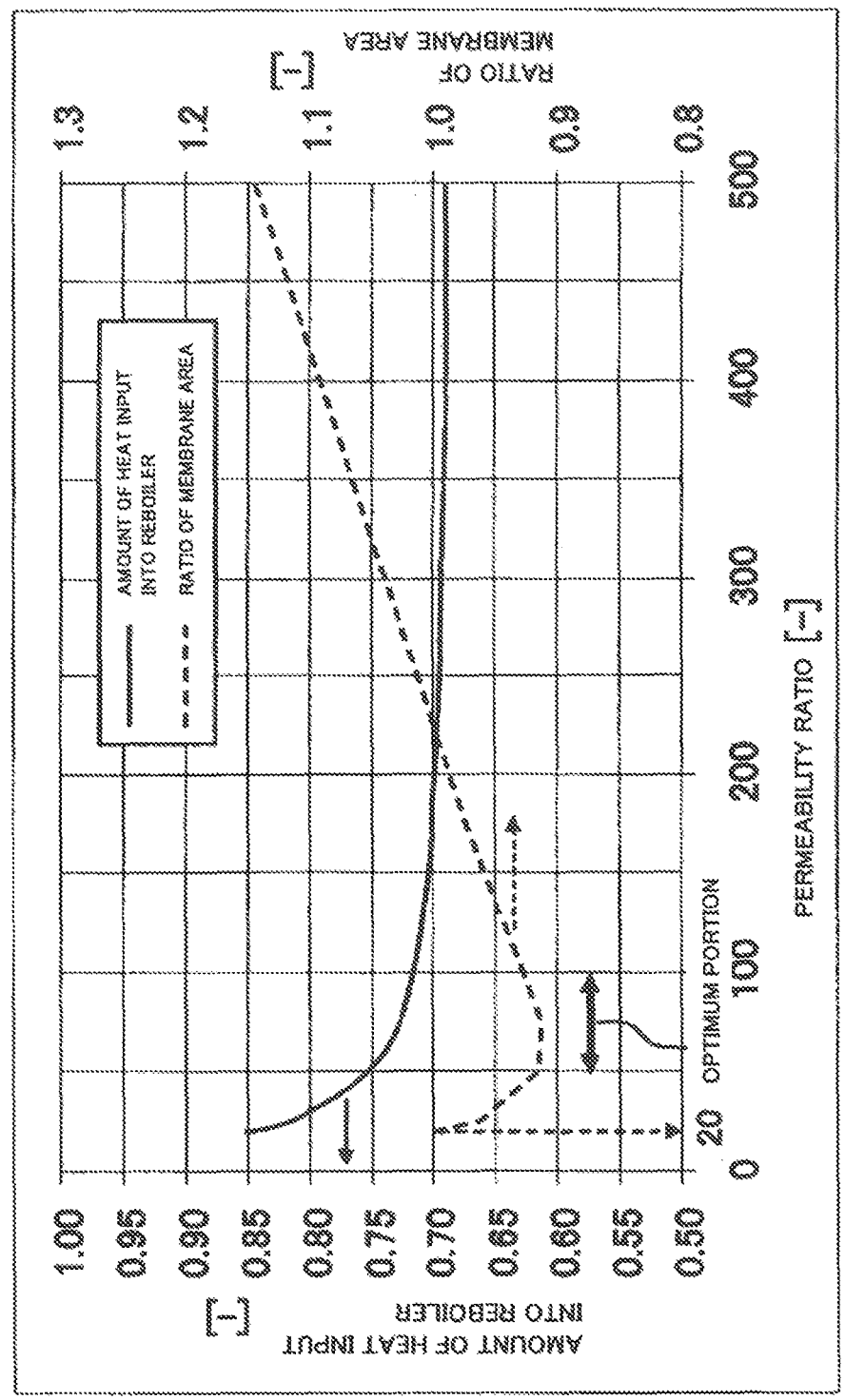
FIG. 5 is a diagram illustrating results in Analysis Example 1.

FIG. 5 is a diagram illustrating results in Analysis Example 1 (the concentration of IPA at the final outlet on the non-permeation side in the separation membrane device 52 was a desired concentration more than 99.9% by mass). As illustrated in FIG. 5, an optimum portion in which the ratio of membrane area was the smallest appeared in a range of the permeability ratio of about 50 to 100. As the permeability ratio increased, the ratio of membrane area tended to increase after the optimum portion. This tendency was common to FIG. 2. It is considered that such an increase was caused by a small driving force of the last path of the separation membrane device 52 (vapor-permeation separation membrane 5).

The necessary amount of heat input into the reboiler was the largest at the time of permeability ratio=20 (initial value). As the permeability increased, the necessary amount of heat input into the reboiler tended to decrease gradually. This tendency was also common to FIG. 2.

Figure 6:
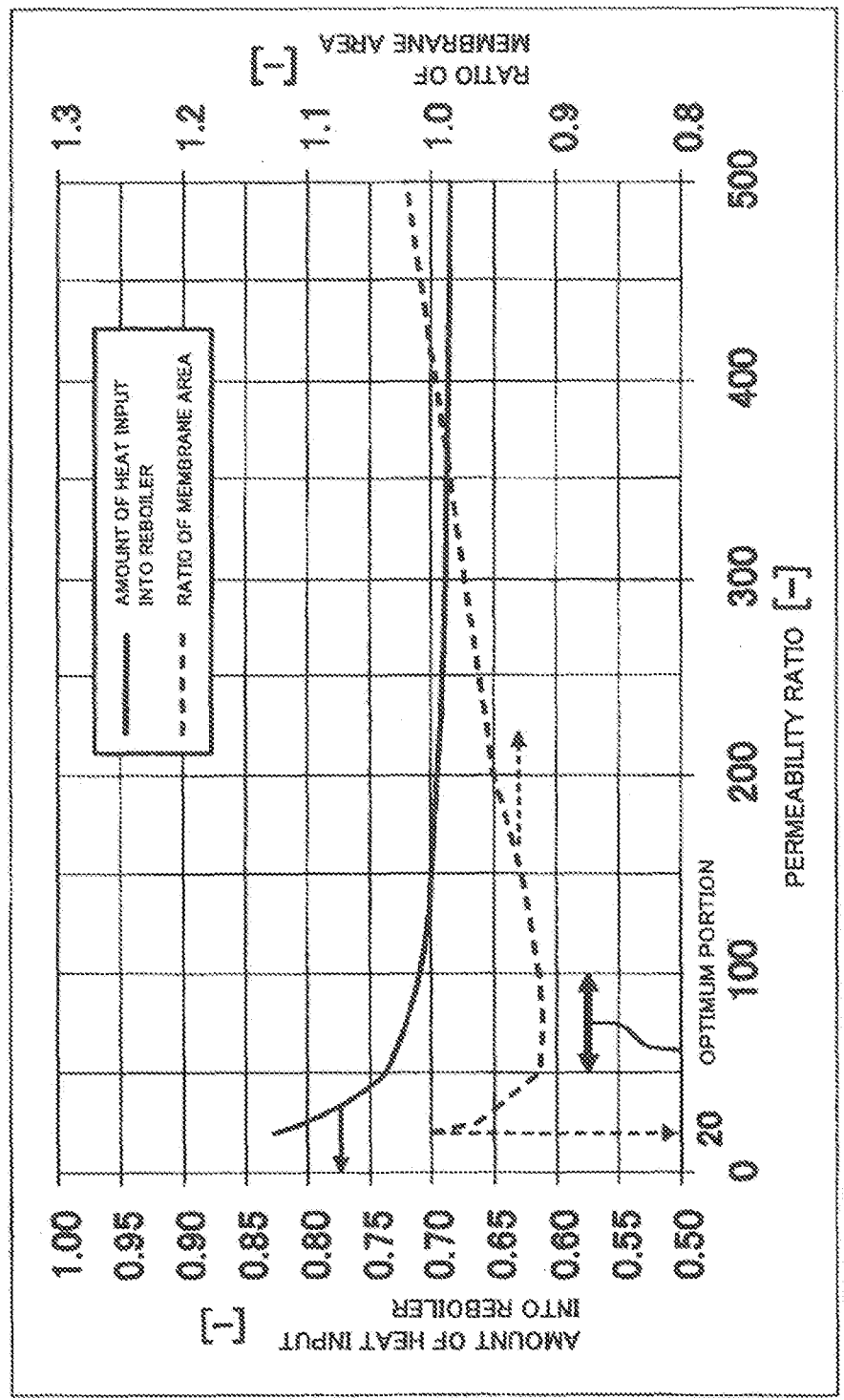
FIG. 6 is a diagram illustrating results in Analysis Example 2.

FIG. 6 is a diagram illustrating results in Analysis Example 2 (the concentration of IPA at the final outlet on the non-permeation side in the separation membrane device 52 was 99.9% by mass). FIG. 6 illustrated a similar tendency to FIG. 5. This tendency was common to FIG. 2.

FIG. 7 is a diagram illustrating results in Analysis Example 3 (the concentration of IPA at the final outlet on the non-permeation side in the separation membrane device 52 was 99.0% by mass). A tendency (appearance of the optimum portion) that the ratio of membrane area became the smallest in a range of the permeability ratio of about 50 to 100, as illustrated in FIGS. 5 and 6, disappeared. As the permeability ratio increased, both the ratio of membrane area and the amount of heat input into the reboiler tended to decrease. This tendency was common to FIG. 3.

As described above, when the concentration of IPA at the final outlet on the non-permeation side in the separation membrane device 52 was more than 99.0% by mass, the ratio of membrane area became the smallest in a range of the permeability ratio of about 50 to 100. As the permeability ratio increased, the ratio of membrane area tended to increase after the smallest portion. An optimum portion appeared in a range of the permeability ratio of 50 to 100.

Example 1

Figure 8:
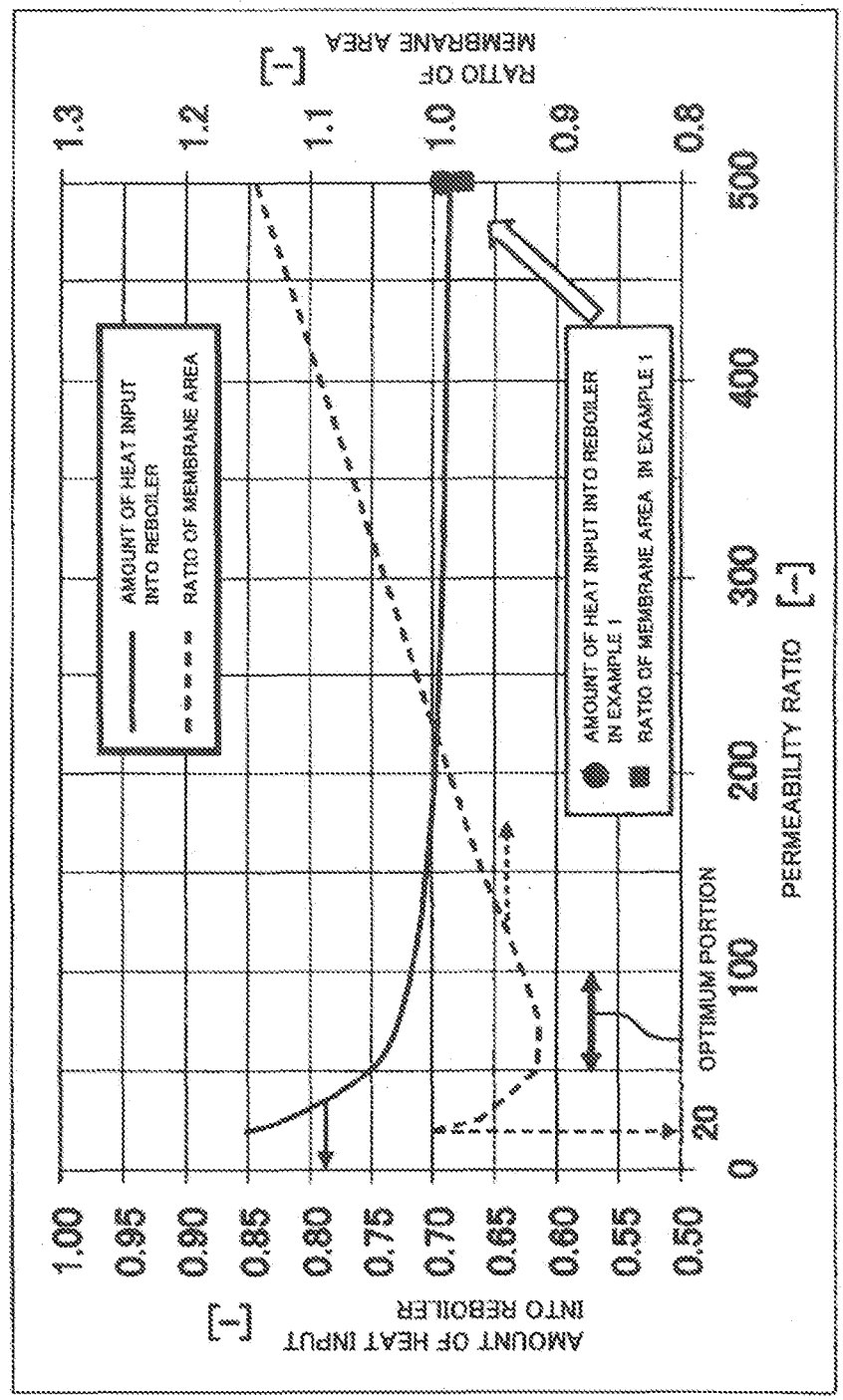
FIG. 8 is a diagram illustrating results in Example 1.

A similar operation to Analysis Example 1 (the concentration of IPA at the final outlet of the separation membrane device 52 was 99.9% by mass or more) was performed using the condensing device 1 illustrated in FIG. 1. In this operation, in the separation membrane devices 51 and 52, a similar separation membrane module to the above-described separation membrane module in Analysis Example 1 was used as the vapor-permeation separation membrane 5. In addition, a vapor-permeation separation membrane 5 having a permeability ratio of 100 was used for the vapor-permeation separation membrane 5 disposed immediately before the final outlet on the non-permeation side in the separation membrane device 52 (only for the last stage (last path) of the four stages (four paths)), and a vapor-permeation separation membrane 5 having a permeability ratio of 500 was used for the other vapor-permeation separation membranes 5. Then, in the case where an operation of condensing IPA was performed according to the above-described (a) distillation step and (b) membrane separation step, the amount of heat input into the reboiler of the distillation column with respect to the necessary amount of heat determined in Reference Example 1 (amount of heat input into the reboiler) and the ratio of a membrane area with respect to the membrane area in the case of permeability ratio=20 (ratio of membrane area) were subjected to simulation analysis using a process simulation software. Results thereof were compared with the results in the case in which all the vapor-permeation separation membranes 5 had a permeability ratio of 500 in Analysis Example 1. The results are shown in FIG. 8 and Table 1.

(Results)

TABLE 1

|  | Example 1 | Analysis Example 1 |
|---|---|---|
| Amount of heat input into reboiler | 0.69 | 0.68 |
| In the case where the value in Analysis Example 1 is defined as 1.0 | 1.01 | — |
| Ratio of membrane area | 0.98 | 1.14 |
| In the case where the value in Analysis Example 1 is defined as 1.0 | 0.86 | — |

FIG. 8 is a diagram illustrating results in Example 1, and illustrates a relation between a permeability ratio and an amount of heat input into the reboiler and a relation between a permeability ratio and a ratio of membrane area of the vapor-permeation separation membrane. As illustrated in FIG. 8 and Table 1, it was possible to confirm that the condensing operation in Example 1 obtained a lower ratio of membrane area than the result in Analysis Example 1, leading to reduction in the membrane area. In the condensing operation in Example 1, the condensing device 1 illustrated in FIG. 1 was used, and a vapor-permeation separation membrane 5 having a permeability ratio of 100 was used for the vapor-permeation separation membrane 5 disposed immediately before the final outlet on the non-permeation side in the separation membrane device 52. In addition, as described above, it was possible to confirm that the amount of heat input into the reboiler was almost the same even when the ratio of membrane area was reduced and energy saving performance could be maintained.

INDUSTRIAL APPLICABILITY

For example, the present invention can be used advantageously as a means for dehydrating and condensing a highly concentrated water-soluble organic matter from a mixture of water and a water-soluble organic matter such as isopropanol, and has extremely high industrial applicability.

REFERENCE SIGNS LIST

1 Device for condensing water-soluble organic matter
2 Distillation column
3 Heat exchanger
4 Junction
5 Vapor-permeation separation membrane
51, 52 Separation membrane device
10 Cooler
11 Condenser drum
12, 13 Vacuum pump
14, 15 Cooler
16 Reboiler
17 Cooler
18, 19 Pump
20, 21 Collecting unit
A to M Path

The invention claimed is:

1. A method for condensing a water-soluble organic matter by distillation and membrane separation, comprising:
distilling a raw material wherein said raw material includes a mixture of water and a water-soluble organic matter having a lower boiling point than water or a mixture of water and a water-soluble organic matter which forms an azeotrope with water and the azeotrope of which with water has a lower boiling point than water, said distillation producing a column top vapor after inputting the raw material into a distillation column; and
introducing said column top vapor obtained in the distillation step into a separation membrane device comprising a first separation membrane device and a second separation membrane device as a subsequent stage thereof, each of the first separation membrane device and the second separation membrane device having a plurality of stages of vapor-permeation separation membranes through which water vapor goes selectively, and obtaining the water-soluble organic matter having a required concentration of more than 99.0% by mass from a final outlet on a non-permeation side in the separation membrane device comprising the first separation membrane device and the second separation membrane device by membrane separation of the vapor-permeation separation membrane, wherein in the vapor-permeation separation membranes of the second separation membrane device, when the permeability of water is referred to as $K_W$ mol/m²·Pa·s and the permeability of the water-soluble organic matter is referred to as $K_A$ mol/m²·Pa·s in the vapor-permeation separation membrane, the permeability ratio $K_W/K_A$ of a vapor-permeation separation membrane disposed at least immediately before the final outlet on the non-permeation side in the separation membrane device comprising the first separation membrane device and the second separation membrane device is lower than those of the other vapor-permeation separation membranes, and wherein the vapor-permeation separation membrane disposed at least immediately before the final outlet on the non-permeation side in the separation membrane device has a portion having a minimum membrane area in a range of the permeability ratio of 50 to 100.

2. The method for condensing a water-soluble organic matter according to claim 1, wherein the vapor-permeation separation membrane having a lower permeability ratio than the other vapor-permeation separation membranes is disposed in a predetermined range of ⅛ to ½ from the final outlet on the non-permeation side in the separation membrane device of the whole of the plurality of stages of vapor-permeation separation membranes.

3. The method for condensing a water-soluble organic matter according to claim 1, wherein the vapor-permeation separation membrane having a lower permeability ratio than the other vapor-permeation separation membranes condenses a water-soluble organic matter in the separation membrane device from an intermediate concentration of 99.0% by mass or more to the required concentration.

4. The method for condensing a water-soluble organic matter according to claim 1, wherein the vapor-permeation separation membrane having a lower permeability ratio than the other vapor-permeation separation membranes has a higher permeability of water than those of the other vapor-permeation separation membranes.

5. The method for condensing a water-soluble organic matter according to claim 1, wherein at least a part of permeation components of the separation membrane device is introduced into the distillation column.

6. The method for condensing a water-soluble organic matter according to claim 1, wherein the required concentration of the water-soluble organic matter obtained from the final outlet on a non-permeation side in the separation membrane device comprising the first separation membrane device and the second separation membrane device is 99.9% by mass or more.

7. The method for condensing a water-soluble organic matter according to claim 1, wherein the water-soluble organic matter is at least one selected from the group consisting of isopropanol, ethanol, methanol, and butanol.

8. The method for condensing a water-soluble organic matter according to claim 1, wherein the permeability ratio $K_W/K_A$ of the vapor-permeation separation membrane disposed at least immediately before the final outlet on the non-permeation side in the separation membrane device comprising the first separation membrane device and the second separation membrane device is 50 to 200 and the permeability ratio $K_W/K_A$ of the other vapor-permeation separation membranes are 200 to 500.

* * * * *